(12) United States Patent
Matsuya (10) Patent No.: US 7,888,057 B2
(45) Date of Patent: Feb. 15, 2011

(54) IMMUNOLOGICAL ASSAY FOR PLASMIN-DIGESTED PRODUCTS OF STABILIZED FIBRIN

(75) Inventor: Takeshi Matsuya, Tokyo (JP)

(73) Assignee: Mitsubishi Chemical Medience Corporation, Tokyo (JP)

( * ) Notice: Subject to any disclaimer, the term of this patent is extended or adjusted under 35 U.S.C. 154(b) by 499 days.

(21) Appl. No.: 11/912,474

(22) PCT Filed: Apr. 27, 2006

(86) PCT No.: PCT/JP2006/308840

§ 371 (c)(1),
(2), (4) Date: Oct. 24, 2007

(87) PCT Pub. No.: WO2006/118195

PCT Pub. Date: Nov. 9, 2006

(65) Prior Publication Data

US 2009/0068682 A1 Mar. 12, 2009

(30) Foreign Application Priority Data

Apr. 28, 2005 (JP) .............................. 2005-132444

(51) Int. Cl.
*G01N 33/53* (2006.01)
(52) U.S. Cl. .................. 435/7.9; 435/7.1; 435/7.92; 435/7.94; 435/287.1; 435/810; 435/975
(58) Field of Classification Search ............. 435/7.1, 435/7.9, 7.92, 7.94, 287.1, 287.7, 810, 975; 422/61
See application file for complete search history.

(56) References Cited

U.S. PATENT DOCUMENTS 5,821,068 A * 10/1998 Soe et al. .................... 435/7.21
6,689,576 B2 * 2/2004 Matsuno et al. ............... 435/21

FOREIGN PATENT DOCUMENTS

EP 0347933 12/1989
JP 2003315338 6/2003

OTHER PUBLICATIONS

Mirshahi et al., Thrombosis Research. 1986. 44(6):715-728.*
Soe et al., Fibrinolysis. 1996. vol. 10, No. Suppl. 4, p. 20.*

(Continued)

*Primary Examiner*—Bao-Thuy L Nguyen
(74) *Attorney, Agent, or Firm*—Heslin Rothenberg Farley & Mesiti, P.C.

(57) ABSTRACT

A method of immunologically analyzing plasmin-digested products of stabilized fibrin, characterized by using a combination of a monoclonal antibody (a) which does not react with stabilized fibrin, fibrinogen, and plasmin-digested products of fibrinogen, but reacts with a neoantigen which is newly exposed in a D domain by digesting stabilized fibrin with plasmin, and a monoclonal antibody (b) which recognizes a site different from that recognized by the monoclonal antibody (a), and specifically reacts with plasmin-digested products of stabilized fibrin, wherein one of the monoclonal antibodies (a) and (b) is carried on a magnetic particle, and the other is labeled with an enzyme, and a chemiluminescent substrate is used as a substrate for the enzyme, is disclosed.

8 Claims, 2 Drawing Sheets

OTHER PUBLICATIONS

Carl-Erik Dempfle, "Validation, Calibration, and Specificity of Quantitative D-Dimer Assays", Seminars in Vascular Medicine, vol. 5(4), Nov. 2005, 315-320.

Carl-Erik Dempfle, "Use of D-Dimer Assays in the Diagnosis of Venous Thrombosis", Seminars in Thrombosis and Hemostatis, vol. 26(6), 2000, 631-641.

Stegnar et al., "Progressive Exposure of E-Neoantigen Associated with Degradation of Crosslinked Fibrin by Plasmin in Vitro", Thrombosis and Haemostasis, vol. 52(3), 1984, 315-320.

Venita C. Eggerding, "Clinical Utility of a Homogenous D-Dimer Assay, as Compared to Two Different ELISA Assays", Blood, vol. 98(11) Part 2, Nov. 16, 2001, Abstract No. 3949, 80b.

Takeshi Matsumoto et al., "Elevated plasma levels of fibrin degradation products by granulocyte-derived elastase (GE-XDP) in patients with disseminated intravascular coagulation (DIC)", Blood, vol. 102(11),Nov. 16, 2003, p. 92b, Abstract No. 4075.

Piia Von Lode, "Point-of-care immunotesting: Approaching the analytical performance of central laboratory methods", Clinical Biochemistry, vol. 38(7), 2005, 591-606.

Irena Bronstein, "1,2-Dioxetanes: Novel Chemiluminescent Enzyme Substrates. Applications to Immunoassays", Journal of Bioluminescence and Chemiluminescence, vol. 4(1), 1989, 99-111.

Susanne A. Pfitzner et al., "Fibrin Detected in Plasma of Patients with Disseminated Intravascular Coagulation by Fibrin-specific Antibodies Consists Primarily of High Molecular Weight Factor XIIIa-crosslinked and Plasmin-modified Complexes Partially Containing Fibrinopeptide A", Thrombosis and Haemostasis, vol. 78(3), 1997, 1069-78.

Supplementary European Search Report for corresponding European application 06745768.9.

Bounameaux et al., "Plasma Measurement of D-Dimer as Diagnostic Aid in Suspected Venous Thromboembolism: An Overview", Thrombosis and Haemostasis, Germany, 1994, vol. 71(1), 1-6.

Bounameaux et al., "D-Dimer testing in suspected venous thromboembolism: an update", Quality Journal of Medicine, United Kingdom, 1997, vol. 90, 437-442.

Wells et al., "Application of a Diagnostic Clinical Model for the Management of Hospitalized Patients with Suspected Deep-vein Thrombosis*", Thrombosis and Haemostasis, Germany, 1999, vol. 81, 493-497.

Van Der Graaf et al., "Exclusion of Deep Venous Thrombosis with D-Dimer Testing", Thrombosis and Haemostasis, Germany, 2000, vol. 83, 191-198.

Matsuda et al., "A Monoclonal Antibody that Recognizes the NH2-Terminal Conformation of Fragment D", Excepta Medica, Amsterdam, Netherlands, 1990, 43-48.

Preston et al., U.K. National External Quality Assessment Scheme for Blood Coagulation, Report on Survey 142, United Kingdom, May 2004, 1-38.

Roul et al., "Intérêt du dosage des D-Dimères dans les états thrombotiques", Annales de Biologie Clinique, France, 1988, vol. 46, 730-733.

Biomerieux Vidas D-Dimer Package Insert, U.S.A., Sep. 2003, 008120-4.

Stein et al., "D-Dimer for the Exclusion of Acute Venous Thrombosis and Pulmonary Embolism", Annals of Internal Medicine, U.S.A., 2004, 589-602.

C. E. Dempfle, "D-dimer testing and venous thromboembolism: four view points", Journal of Thrombosis and Haemostasis, United Kingdom, 2005, 377-384.

"The diagnosis of deep vein thrombosis in symptomatic outpatients and the potential for clinical assessment and D-dimer assays to reduce the need for diagnostic imaging", © 2004 Blackwell Publishing Ltd., British Journal of Haematology, United Kingdom, 2004, 15-25.

Mitsuko Himizu, "Study on Clinical Significance of FDP D-dimer Values Assayed by LPIA-100", Japanese Journal of Clinical Laboratory Automation, vol. 16, No. 1, 1991, 59-63, Abstract Only.

* cited by examiner

IMMUNOLOGICAL ASSAY FOR PLASMIN-DIGESTED PRODUCTS OF STABILIZED FIBRIN

CROSS REFERENCE TO RELATED APPLICATIONS

This application is a 371 filing of PCT International application no. PCT/JP2006/308840 filed Apr. 27, 2006 and published in Japanese as WO 2006/118195 on Nov. 9, 2006 which claims the priority of Japanese application no. 2005 132444 filed Apr. 28, 2005. The disclosures of these applications and all other patents, published applications and other references cited herein are hereby incorporated by reference in their entirety.

TECHNICAL FIELD

The present invention relates to a method of immunologically analyzing plasmin-digested products of stabilized fibrin, particularly, a highly sensitive assay for plasmin-digested products of stabilized fibrin by chemiluminescence.

The term "analysis" as used herein includes a detection to determine a presence or absence of a substance to be analyzed, and a measurement to quantitatively or semi-quantitatively determine an amount or activity of a substance to be analyzed.

BACKGROUND ART

Digested products of human stabilized fibrin with various proteases are useful as diagnostic markers in clinical diagnosis. For example, plasmin-digested products of human stabilized fibrin, which include p-DD/E as a base unit, and polymers or oligomers thereof (hereinafter sometimes referred to as D-D dimer or DD/E complex), are widely used as a diagnostic marker of disseminated intravascular coagulation (DIC). In a determination of the plasmin-digested products of stabilized fibrin in a biological sample, an agglutination of latex sensitized with a monoclonal antibody specific to the plasmin-digested products of stabilized fibrin is generally used.

Deep vein thrombosis (DVT) is now in need of attention. DVT has not been greatly noted in Japan, but the number of patients suffering therefrom is increasing as the westernization of Japanese life style proceeds. A diagnosis or prediction of thrombosis or the presence of thrombi is extremely difficult, but the plasmin-digested products of stabilized fibrin is the most reliable marker for a DVT diagnosis (nonpatent references 1 and 2). Stabilized fibrin, which is generated by crosslinking fibrin during a coagulation process, is digested with plasmin to covert p-DD/E polymers or oligomers composed of the p-DD/E base unit, or p-DD/E. Therefore, the formation of thrombus and the secondary fibrinolysis may be monitored by detecting p-DD/E or the polymers or oligomers thereof. The measurement of the plasmin-digested products of stabilized fibrin is very useful in confirming the presence of thrombi.

Pulmonary embolism (PE), known as the economy-class syndrome, has come to the fore. PE is considered to be developed by blocking the blood flow with deep vein thrombi that pass through the inferior vena cava and pulmonary heart and reach a pulmonary artery. There is a report that the measurement of the plasmin-digested products of stabilized fibrin is useful in evaluating patients suffering from PE as well as those with DVT (nonpatent references 3 and 4).

A monoclonal antibody JIF-23 is known as a monoclonal antibody capable of specifically detecting the plasmin-digested products of stabilized fibrin (nonpatent reference 5). It is known that this antibody recognizes the N-terminal structure newly exposed in the $D_1$ domain after liberating the N-terminal sequence consisting of amino acids 63-85 in the γ chain of the $D_{1A}$ domain in the plasmin-digested products of human stabilized fibrin therefrom. The formation of thrombus and the secondary fibrinolysis can be easily monitored by a measuring method capable of specifically analyzing the plasmin-digested products of stabilized fibrin contained in a biological sample using the antibody JIF-23. Such a measuring method is not particularly limited, but may be, for example, a latex agglutination method or an ELISA method.

A latex agglutination method is known in the clinical field as a commonly-used conventional method of measuring the plasmin-digested products of stabilized fibrin using the antibody JIF-23. The amount of the plasmin-digested products of stabilized fibrin is 0.4 µg/mL FEU in healthy persons according to nonpatent reference 6, and 15.2±18.5 µg/mL in patients suffering from DIC according to nonpatent reference 7. The plasmin-digested products of stabilized fibrin can be detected with the latex agglutination reaction using the antibody JIF-23 (sensitivity of detection=approximately 45 ng/mL) and, in fact, this method is commonly used in the clinical field.

The clinical cut-off value for DVT is 0.5 µg/mL FEU according to nonpatent reference 8. The diagnosis of DVT requires monitoring slight changes between values of healthy persons and patients in comparison with the diagnosis of DIC, and therefore, a more sensitive measuring method capable of accurately assaying the plasmin-digested products of stabilized fibrin in the normal range is desired.

As an ELISA method using an antibody that recognizes a neoantigen in the D domain of the digested products of stabilized fibrin, for example, MiniVidas (Biomerieux) is known (nonpatent references 8 and 11). It is reported in nonpatent reference 9 that the sensitivity in an ELISA method is higher than that in a latex agglutination, and thus, the ELISA method is useful in the diagnosis of DVT. Such an ELISA method with a high sensitivity is spreading to the clinical field as a method of measuring the plasmin-digested products of stabilized fibrin. For example, the detection sensitivity of the MiniVidas is approximately 45 ng/mL FEU.

The values and units as described above are based on the descriptions of the nonpatent references, and the units "µg/mL FEU" and "µg/mL" can be interconverted according to the following equation:

1 µg/mL=2 µg/mL FEU wherein the value "2" is an approximate value (nonpatent reference 10).

[non-patent reference 1] Thrombosis and Haemostasis, Germany, 1994, vol. 71, p. 1-6

[non-patent reference 2] Quality Journal of Medicine, United Kingdom, 1997, vol. 90, p. 437-442

[non-patent reference 3] Thrombosis and Haemostasis, Germany, 1999, vol. 81, p. 493-497

[non-patent reference 4] Thrombosis and Haemostasis, Germany, 2000, vol. 83, 191-198

[non-patent reference 5] Excepta Medica, Amsterdam, Netherlands, 1990, p. 43-48

[non-patent reference 6] U.K. National External Quality Assessment Scheme for Blood Coagulation, Report on Survey 142, United Kingdom, May, 2004

[non-patent reference 7] ANNALES DE BIOLOGIE CLINIQUE, France, 1988, vol. 46, p. 730-733

[non-patent reference 8] Biomerieux Vidas D-Dimer Package Insert, U.S.A., September, 2003, 008120-4

[non-patent reference 9] Annals of Internal Medicine, U.S.A., 2004, p. 589-602

[non-patent reference 10] Journal of Thrombosis and Haemostasis, United Kingdom, 2005, p. 377-384

[non-patent reference 11] British Journal of Haematology, United Kingdom, 2004, p. 15-25

DISCLOSURE OF THE INVENTION

Problems to be Solved by the Invention

An object of the present invention is to provide a more sensitive assay for plasmin-digested products of stabilized fibrin. Such an assay, with a sensitivity higher than those of conventional highly sensitive assays, allows for a reduction in a measuring time.

Means for Solving the Problems

The object can be solved by the present invention, that is, a method of immunologically analyzing plasmin-digested products of stabilized fibrin, characterized by using a combination of (a) a monoclonal antibody which does not react with stabilized fibrin, fibrinogen, and plasmin-digested products of fibrinogen, but reacts with a neoantigen which is newly exposed in a D domain by digesting stabilized fibrin with plasmin, and (b) a monoclonal antibody which recognizes a site different from that recognized by the monoclonal antibody (a), and specifically reacts with plasmin-digested products of stabilized fibrin, wherein one of the monoclonal antibodies (a) and (b) is carried on a magnetic particle, and the other is labeled with an enzyme, and a chemiluminescent substrate is used as a substrate for the enzyme.

According to a preferred embodiment, the monoclonal antibody (b) does not react with stabilized fibrin, fibrinogen, and plasmin-digested products of fibrinogen, but reacts with a neoantigen that is newly exposed in an E domain by digesting stabilized fibrin with plasmin.

According to another preferred embodiment, the method comprises (1) bringing a sample suspected of containing plasmin-digested products of stabilized fibrin into contact with the monoclonal antibodies (a) and (b);

(2) separating an enzyme-labeled monoclonal antibody which forms an immunocomplex, via plasmin-digested products of stabilized fibrin, with the monoclonal antibody carried on a magnetic particle, from an enzyme-labeled monoclonal antibody which does not form the immunocomplex;

(3) adding a chemiluminescent substrate to the separated immunocomplex of monoclonal antibody carried on a magnetic particle/plasmin-digested products of stabilized fibrin/ enzyme-labeled monoclonal antibody, to cause an emission of chemiluminescent light; and (4) analyzing the generated chemiluminescent signal.

According to still another preferred embodiment, the chemiluminescent substrate is 1,2-dioxetane.

According to still another preferred embodiment, the labeling enzyme is alkaline phosphatase.

The present invention relates to a kit for immunologically analyzing plasmin-digested products of stabilized fibrin, characterized by comprising (a) a monoclonal antibody which does not react with stabilized fibrin, fibrinogen, and plasmin-digested products of fibrinogen, but reacts with a neoantigen which is newly exposed in a D domain by digesting stabilized fibrin with plasmin, (b) a monoclonal antibody which recognizes a site different from that recognized by the monoclonal antibody (a), and specifically reacts with plasmin-digested products of stabilized fibrin, and (c) a chemiluminescent substrate, wherein one of the monoclonal antibodies (a) and (b) is carried on a magnetic particle, and the other is labeled with an enzyme a substrate of which is the chemiluminescent substrate The present invention relates to a method of detecting (or diagnosing) deep vein thrombosis and/or pulmonary embolism, characterized by analyzing plasmin-digested products of stabilized fibrin contained in a sample by the immunologically analyzing method or the immunologically analyzing kit.

Effects of the Invention

According to the immunological assay of the present invention, a sensitive and specific analysis can be performed for the plasmin-digested products of stabilized fibrin. The present invention can be applied to diagnosis of DVT and/or pulmonary embolism as well as DIC.

BEST MODE FOR CARRYING OUT THE INVENTION

The term "plasmin-digested products of stabilized fibrin" as used herein means digested products that are generated by digesting stabilized fibrin with plasmin and are substantially composed of one or plural base units p-DD/E. The plasmin-digested products of stabilized fibrin include p-DD/E as the above base unit, and p-DD/E polymers or oligomers consisting of plural base units. The plasmin-digested products of stabilized fibrin are sometimes referred to as, for example, D-D dimer or DD/E complex.

In the present specification, a digestion product generated by digestion with plasmin is sometimes denoted by placing the symbol "p-" in front of the product. Similarly, a digestion product generated by digestion with granulocyte elastase is sometimes denoted by placing the symbol "e-" in front of the product.

In the present invention including the immunologically analyzing method (i.e., immunological assay) of the present invention and the immunologically analyzing kit of the present invention, two different monoclonal antibodies that recognize different epitopes are used as monoclonal antibodies. The term "antibody" as used herein means not only the full length of the antibody, but also a fragment of the antibody. As the antibody fragment, there may be mentioned, for example, Fab, Fab', F(ab')$_2$, or Fv. An antibody to specifically detect the plasmin-digested products of human stabilized fibrin in a sandwich immunoassay should not form a sandwich immunocomplex with stabilized fibrin, fibrinogen, or plasmin-digested products of fibrinogen, but react, as an epitope, with a site (i.e., neoantigen) which is newly exposed in digested products by digesting stabilized fibrin with plasmin to form a sandwich immunocomplex.

In the present invention, a monoclonal antibody which does not react with stabilized fibrin, fibrinogen, and plasmin-digested products of fibrinogen, but reacts with a neoantigen which is newly exposed in a D domain by digesting stabilized fibrin with plasmin is used as the first monoclonal antibody (hereinafter sometimes referred to as anti-D-domain-neoantigen antibody), and a monoclonal antibody which recognizes a site different from that recognized by the first monoclonal antibody, and specifically reacts with plasmin-digested products of stabilized fibrin is used as the second monoclonal antibody.

The first antibody (i.e., the anti-D-domain-neoantigen antibody) used in the present invention is not particularly limited, so long as it is a monoclonal antibody which recognizes a neoantigen which is newly exposed in a D domain by digesting stabilized fibrin with plasmin. As the first antibody, for example, a monoclonal antibody which recognizes a neoantigen which is newly exposed in a D domain when a fragment consisting of amino acids 63-85 of the γ chain is released from the γ chain by digesting stabilized fibrin with plasmin, such as monoclonal antibody JIF-23, may be used.

The antibody JIF-23 is a well-known monoclonal antibody which may be used to specifically detect the plasmin-digested products of stabilized fibrin (for example, Matsuda, M., Terukina, S., Yamazumi, K., Maekawa, H., Soe, G., A monoclonal antibody that recognizes the NH2-terminal conformation of fragment D, Excerpta Medica, Amsterdam; 1990, 43-38). The antibody JIF-23 reacts with not only the plasmin-digested products of stabilized fibrin, but also granulocyte-elastase-digested products of stabilized fibrin (i.e., e-DD/E as a base unit, and polymers or oligomers thereof). Because the p-DD/E as the base unit of plasmin-digested products of stabilized fibrin contains two epitopes of the antibody JIF-23, the plasmin-digested products of stabilized fibrin can be specifically detected by using the antibody JIF-23 alone, and a latex reagent for measuring the plasmin-digested products of stabilized fibrin using the antibody JIF-23 is widely used in the clinical field.

In the present invention, the second antibody which recognizes a site different from that recognized by the first antibody such as the antibody JIF-23 is used together with the first antibody to construct a system for detecting the plasmin-digested products of stabilized fibrin. The second antibody is not particularly limited, so long as it specifically recognizes an amino acid sequence or a tertiary structure thereof which is newly exposed by digesting stabilized fibrin with plasmin. As the second antibody, there may be mentioned, for example, a monoclonal antibody which specifically recognizes a neoantigen in the E domain (for example, monoclonal antibodies No. 36-1, No. 1-1, and No. 5-4), monoclonal antibody DD3B6/22 (American Diagnostica; Thrombosis Research, 1983, vol. 31, p. 87-96 or Drug Coagulation & Fibrinolysis, 1997, vol. 8, p. 87-96), monoclonal antibody MA8D3 (IL etc.; Thrombosis and Haemostasis, 1989, vol. 58, p. 1024-1029), monoclonal antibody P10B5E12C9 (Biomerieux; Clinical Chemistry, 1996, vol. 42, p. 410-415), or monoclonal antibody P2C5A10 (Biomerieux; Clinical Chemistry, 1996, vol. 42, p. 410-415).

The monoclonal antibody which specifically recognizes a neoantigen in the E domain (hereinafter referred to as anti-E-domain-neoantigen antibody), which may be used as the second antibody, is not particularly limited, so long as it is a monoclonal antibody which does not react with stabilized fibrin, fibrinogen, and plasmin-digested products of fibrinogen, but reacts with a neoantigen which is newly exposed in the E domain by digesting stabilized fibrin with plasmin. As the anti-E-domain-neoantigen antibody, for example, antibodies having reaction specificities listed in Table 1 of Referential Example 1, such as monoclonal antibodies No. 36-1, No. 1-1, and No. 5-4, may be used. The antibody No. 36-1 reacts with the plasmin-digested products of stabilized fibrin, but does not react with the granulocyte-elastase-digested products of stabilized fibrin.

In the present invention, one of the two monoclonal antibodies is carried on magnetic particles, and the other is labeled with an enzyme. The magnetic particle used in the present invention is not particularly limited, so long as it has magnetic properties and may be used as a solid carrier for immunoreaction. The magnetic particle may be prepared from a polymer which is impregnated with a magnetizable substance. The surface of the particle is not particularly limited, so long as an antibody may be immobilized on the surface. When an antibody is immobilized by physical adsorption, the surface of the particle is preferably hydrophobic. When an antibody is immobilized by chemical bonding, it is preferable to introduce a functional bond, such as a carboxyl, succinimide, isothiocyanate, chlorosulfonyl, maleimide, hydrazide, amino, or SH group, into the surface of the particle. The particle diameter of the magnetic particle may be, for example, 0.1 to 10 μm, preferably 1 to 5 μm.

An antibody may be immobilized on magnetic particles by a conventional method, such as a physical adsorption method based on a hydrophobic interaction or a chemically binding method. When the chemically binding method is used, for example, a carboxyl, succinimide, isothiocyanate, chlorosulfonyl, maleimide, hydrazide, or amino group may be used. In the case of the carboxyl group, carbodiimide is used to activate a carboxyl group, which may bind to an amino group of an antibody. The succinimide, isothiocyanate, or chlorosulfonyl group may directly react with an amino group of an antibody. The maleimide group may react with, for example, an SH group. The SH group may be introduced into an antibody by using an SH introduction reagent. Alternatively, the SH group at the hinge site of an antibody may be used by reducing the antibody. The hydrazide group may react with sugar chains of an antibody. In the case of the amino group, glutaraldehyde may be used to convert an amino group on the particle to an aldehyde group, which may react with an amino group of an antibody.

The enzyme used to label the monoclonal antibody in the present invention is not particularly limited, so long as chemiluminescence is applicable. A highly sensitive analysis can be performed by using such an enzyme. When a substrate is luminol, peroxidase may be used as the labeling enzyme. When a substrate is lumigen PPD, alkaline phosphatase may be used as the labeling enzyme. A combination of alkaline phosphatase as the enzyme and 1,2-dioxetane [particularly, CDP-Star (Tropics)] as the substrate is useful and preferable, from the viewpoint of the S/N ratio. As is the case with AMPPD or CSPD, CDP-Star is hydrolyzed by alkaline phosphatase to cause light emission via an intermediate. It has been reported that the light intensity of CDP-Star is extremely high in comparison with those of AMPPD and CSPD [Bronstein, I., Edwards, B., Voyta, J. C., 1,2-Dioxetanes: Novel Chemiluminescent Enzyme Substrates. Application to Immunoassays, Journal of Bioluminescence and Chemiluminescence; 4, 99-111 (1989); Beck, S., Koster, H., Applications of Dioxetane Chemiluminescent Probes to Molecular Biology, Analytical Chemistry; 62, 2258-2270 (1990); Tizard, R., Cate, R. L., Ramachandran, K. L., Wysk, M., Voyta, J. C., Murphy, O. J., Bronstein, I., Imaging of DNA Sequences with Chemiluminescence, Proc. Natl. Acad. Sci. USA.; 87, 4514-4518 (1990); or Bronstein, I., Voyta, J. C., Lazzari, K. G., Murphy, O., Edwards, B., Kricka, L. J., Rapid and Sensitive Detection of DNA in Southern Blots with Chemiluminescence, BioTechniques; 8, 310-314 (1990)]. Further, CDP-Star is advantageous as a substrate for a highly sensitive assay using alkaline phosphatase, because the rise time of chemiluminescence by CDP-Star is more rapid than those of AMPPD and CSPD, and the chemiluminescence is maintained for more than 24 hours.

An antibody may be labeled with the enzyme by a conventional method. As such a conventional method, there may be mentioned, for example, a method of crosslinking an amino group of the enzyme with an amino group of the antibody by using glutaraldehyde; a method in which a functional group (such as a succinimide or isothiocyanate group) capable of binding to an amino group is introduced into the enzyme via an amino acid of the enzyme, and is reacted with an amino group of the antibody; or a method in which a maleimide group is introduced into the enzyme via an amino acid of the enzyme, and is reacted with an SH group or the like at the hinge site of the antibody. When the enzyme is a glycoprotein such as horseradish peroxidase, sugar chains of the enzyme may be converted by periodic acid to an aldehyde group, which may react with an amino group of the antibody.

The immunologically analyzing method of the present invention may be carried out in accordance with conventional immunoassays, for example, manually or by using an automated system, except that a combination of specific monoclonal antibodies is used. More particularly, a sample to be assayed or a standard sample, a monoclonal antibody carried on magnetic particles, and another monoclonal antibody labeled with an enzyme are brought into contact with each other in a reaction tube, and the mixture is incubated at a predetermined temperature (for example, at 30 to 40° C.). A magnet is placed on the outer wall of the reaction tube to capture the antibody-carrying magnetic particles on the inner wall of the reaction tube. The inside of the reaction tube is washed while capturing the particles. A chemiluminescent substrate is added to the reaction tube to cause light emission. The resulting light signal is measured to determine an amount of the plasmin-digested products of stabilized fibrin contained in the assay sample or standard sample. Because the separation of particles from the sample liquid after the incubation, and the subsequent separation from the washing liquid can be precisely performed by using the magnetic particles and the magnet, the method is advantageous from the viewpoint of a reduction or the like in a blank. As a sample which may be analyzed by the present invention, there may be mentioned a biological sample suspected of containing the plasmin-digested products of stabilized fibrin, such as blood, plasma, serum, or urine.

The present inventor used a combination of the antibody JIF-23 as the first antibody and the antibody No. 36-1 (an antibody that recognizes a structure newly exposed in the E domain by plasmin digestion) as the second antibody, to evaluate the correlation between the present invention and conventional latex reagents, by measuring the plasmin-digested products of stabilized fibrin contained in human plasma. In (1) a comparison of "a latex agglutination method using the JIF-23 antibody alone" with "a measuring system of antibody-immobilized magnetic particles and an alkaline-phosphatase-labeled antibody using the JIF-23 antibody alone", and (2) a comparison of "the latex agglutination method using the JIF-23 antibody alone" with "a measuring system of JIF-23-antibody-immobilized magnetic particles and an alkaline-phosphatase-labeled monoclonal antibody which recognizes the E domain after plasmin digestion", no significant differences were observed in the gradients and intercepts of regression lines and correlation coefficients, obtained from the results of correlation tests using human plasma samples (n=50) containing plasmin-digested products of stabilized fibrin. It is considered from this result that the specificity of the measuring system using the combination of the JIF-23 antibody and the antibody which recognizes the structure newly exposed in the E domain after plasmin digestion is not substantially different from that of the measuring system using the JIF-23 antibody alone, in measuring the plasmin-digested products of stabilized fibrin contained in plasma.

According to the Francis et al. report [Francis, C. W., Marder, V. J., Barlow, G. H., Plasmic degradation of crosslinked fibrin, Journal of Clinical Investigation; 66, 1033-1043, 1980], they speculated that the plasmin-digested products of stabilized fibrin might not reach the phase 4 [i.e., the state in which the stabilized fibrin is digested to the DD/E base unit, or the fragment D dimer (DD) and the fragment E] in vivo by the action of the blood flow and an $\alpha_2$ plasmin inhibitor, and might remain in the phase 3 [i.e., the state in which the stabilized fibrin is digested to the polymers or oligomers of the DD/E base units]. Soe et al. reported data that supported their speculation [Soe, G., Kohno I., Sakurai, J., and Matsuda, M., Analysis of plasmin-digested products of fibrin using monoclonal antibody JIF-23 that recognizes the amino terminal structure of fragment D, Japanese Journal of Thrombosis and Haemostasis, 5, 105-113, 1994]. These reports strongly suggest the above result in that no significant difference was observed in the correlations of the above correlation tests (1) and (2).

EXAMPLES

The present invention now will be further illustrated by, but is by no means limited to, the following Examples.

Example 1

Assay of Plasmin-Digested Products of Stabilized Fibrin by Automated System (1) Preparation of Magnetic Particles on which Anti-D-Domain-Neoantigen Monoclonal Antibody JIF-23 is Immobilized An F(ab')$_2$ fraction obtained by digesting the antibody JIF-23 with pepsin was prepared in accordance with the report of Matsuya et al. (Matsuya, T., Tashiro, S., Hoshino, N., Shibata, N., Nagasaki, Y., Kataoka, K., A core-shell-type fluorescent nanosphere possessing reactive PEG tethered chains on the surface for zeptomole detection of protein in time-resolved fluorometric immunoassay; Anal. Chem., 75, 6124-6132, 2003).

To a 1% suspension (10 mL) of carboxyl-group-introduced magnetic particles (particle diameter=2.5 μm; manufactured by JSR) in a 50 mmol/L MES buffer (pH 6.5), an aqueous solution (1 mL) containing 100 mg/mL carbodiimide was added, and the whole was mixed by inverting the reaction tube at room temperature for 1 hour. This mixture was centrifuged at 14000 rpm for 15 minutes to collect the magnetic particles, which were washed twice with a 50 mmol/L MES buffer (pH 6.5). A JIF-23 antibody F(ab')$_2$ solution (200 μg/10 mL) in a 50 mmol/L MES buffer (pH 6.5) was added to the resulting magnetic particles, and the whole was mixed by inverting the tube at room temperature for 1 hour. This mixture was centrifuged at 14000 rpm for 15 minutes to remove the unreacted antibody solution. A 0.3% solution (10 mL) of bovine serum albumin in 0.1 mol/L Tris-HCl (pH 8.0) was added thereto, and the whole was mixed by inverting the tube at room temperature for 30 minutes. This mixture was centrifuged at 14000 rpm for 15 minutes to remove the bovine serum albumin solution. The resulting antibody-immobilized magnetic particles were washed with a 10 mmol/L Tris-HCl buffer (pH 8.0) containing 0.01% Tween-20, and used in the following experimentation.

(2) Preparation of Anti-E-Domain-Neoantigen Monoclonal Antibodies No. 36-1, No. 1-1, and No. 5-4 Labeled with Alkaline Phosphatase Fab' fractions of antibodies No. 36-1, No. 1-1, and No. 5-4 recognizing the E domain after plasmin digestion were carried out in accordance with the report of Matsuya et al. (Matsuya, T., Tashiro, S., Hoshino, N., Shibata, N., Nagasaki, Y., Kataoka, K., A core-shell-type fluorescent nanosphere possessing reactive PEG tethered chains on the surface for zeptomole detection of protein in time-resolved fluorometric immunoassay; Anal. Chem., 75, 6124-6132, 2003). The reaction specificities of the monoclonal antibodies No. 36-1, No. 1-1, and No. 5-4 are shown in Referential Example 1 described below.

The resulting Fab' fractions of the monoclonal antibodies No. 36-1, No. 1-1, and No. 5-4 were labeled with alkaline phosphatase in accordance with the report of Ishikawa et al. [Ishikawa, E., Imagawa, M., Hashida, S., Yoshitake, S., Hamaguchi, Y., & Ueno, T., Enzyme-labeling of antibodies and their fragments for enzyme immunoassay and immunohistochemical staining; J. Immunoassay, 4, 209-327, 1983, and Ishikawa, E., Hashida, S., Kohno, T. & Tanaka, K., Methods for enzyme-labeling of antigens, antibodies and their fragments; In: Nonisotopic Immunoassay, T. T. Ngo (ed.), p 27-55, Plenum Publishing Corporation, New York, 1988].

For comparison, the above procedures were repeated, expect for a use of the antibody JIF-23, to prepare a JIF-23 monoclonal antibody Fab' fraction labeled with alkaline phosphatase.

(3) Preparation of Plasmin-Digested Products of Stabilized Fibrin

Plasmin-digested products of stabilized fibrin were prepared in accordance with the report of Olexa et al. [Olexa, S. A., Budzynski, A. Z., Primary soluble plasmic degradation product of human cross-linked fibrin. Isolation and stoichiometry of the (DD)E complex; Biochemistry, 18, 991-995, 1979]. Fragment D and fragment E, which are degradation products of the plasmin-digested products of stabilized fibrin, were prepared in accordance with the report of Masci et al. [Masci, P. P., Whitaker, A. N., Winzor, D. J., A simple chromatographic procedure for the purification of the D dimmer fragment from crosslinked fibrin; Analytical Biochemistry, 147, 128-135, 1985].

(4) Measurement of Plasmin-Digested Products of Stabilized Fibrin Using Antibody-Immobilized Magnetic Particles and Antibody Labeled with Alkaline Phosphatase A diluted series prepared by diluting the plasmin-digested products of stabilized fibrin with a 20 mmol/L Tris-HCl (pH7.0) buffer containing 3% bovine serum albumin was used as samples. Each sample (50 μL), each alkaline-phosphatase-labeled Fab' fraction (50 μL) of the No. 36-1, No. 1-1, or No. 5-4 antibody, and the magnetic particles (1% magnetic particles, 50 μL) on which the F(ab')$_2$ fraction of the JIF-23 antibody was immobilized were mixed and reacted at 37° C. for 5 minutes. An washing solution containing Triton X-100 as the main component was used to remove unreacted sample components and excess labeled antibodies. The magnetic particles to which the immunocomplex bound were mixed with 100 μL of chemiluminescent substrate CDP-Star (Tropics), and a light signal after 1 minute from the mixing was measured using a photomultiplier.

For comparison, the above procedure was repeated, except that the alkaline-phosphatase-labeled Fab' fraction of the JIF-23 antibody was used instead of the alkaline-phosphatase-labeled Fab' fraction of the No. 36-1 antibody.

(5) Results of Measuring Plasmin-Digested Products of Stabilized Fibrin

Figure 1:
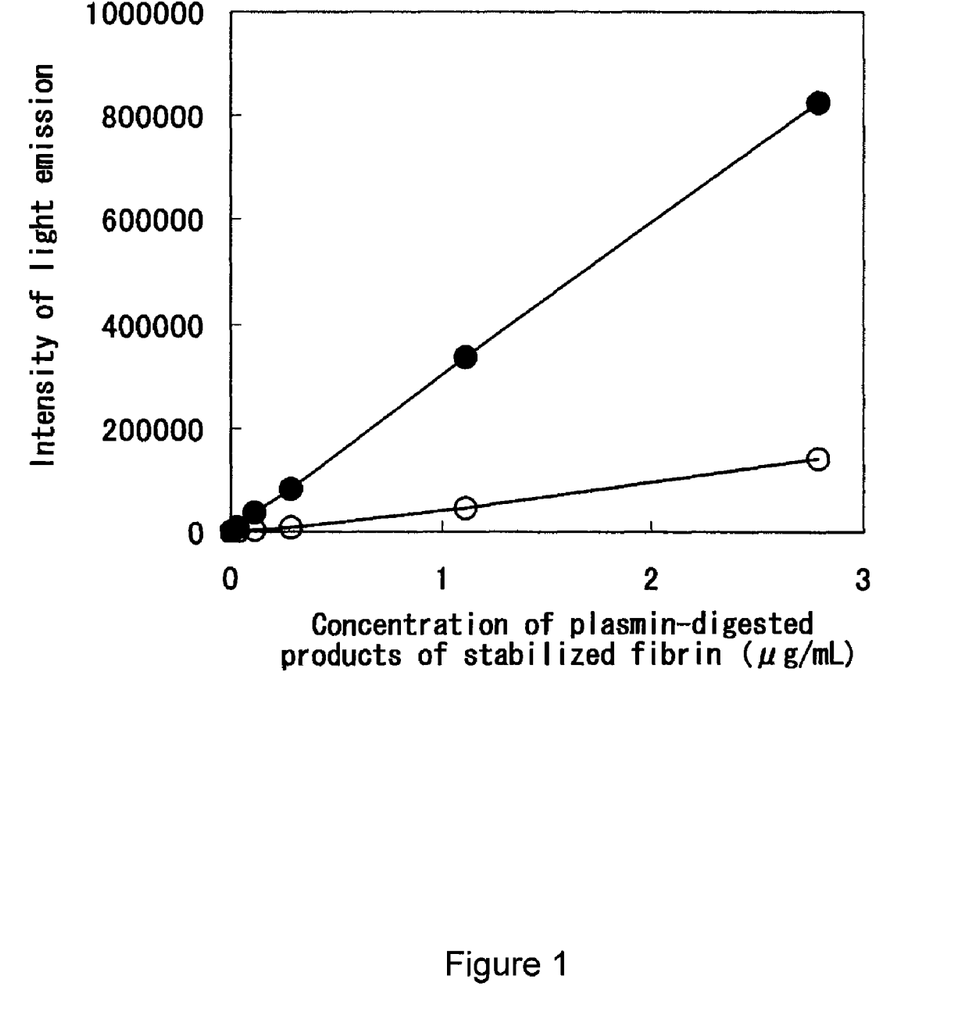
FIG. 1 is a graph showing the results of measuring a diluted series of plasmin-digested products of stabilized fibrin using two measuring systems, that is, one embodiment of the method of the present invention using a combination of the JIF-23-antibody-immobilized magnetic particles and the alkaline-phosphatase-labeled No. 36-1 antibody (solid circles) and a method for comparison using a combination of the JIF-23-antibody-immobilized magnetic particles and the alkaline-phosphatase-labeled JIF-23 antibody (open circles).

FIG. 1 shows the results of measuring a diluted series of plasmin-digested products of stabilized fibrin using two measuring systems, that is, one embodiment of the method of the present invention using a combination of the JIF-23-antibody-immobilized magnetic particles and the alkaline-phosphatase-labeled No. 36-1 antibody (solid circles in FIG. 1) and a method for comparison using a combination of the JIF-23-antibody-immobilized magnetic particles and the alkaline-phosphatase-labeled JIF-23 antibody (open circles in FIG. 1).

When two different monoclonal antibodies (i.e., JIF-23 and No. 36-1 antibodies) that recognized different epitopes were used, the reactivity of this measuring system to the plasmin-digested products of stabilized fibrin was enhanced by approximately 6-fold, in comparison with the measuring system using the JIF-23 antibody alone. The detection sensitivity of this measuring system was 0.005 μg/mL FEU (assay time=approximately 17 minutes), and was enhanced by approximately 9-fold, in comparison with the detection sensitivity (45 ng/mL FEU, assay time=approximately 35 minutes) of a conventional ELISA method (MiniVidas; Biomerieux, nonpatent references 8 and 11) using an antibody that recognized a neoantigen in the D domain of digested products of stabilized fibrin. The high sensitivity in the method of the present invention also contributed to a shortening of the assay time.

Figure 2:
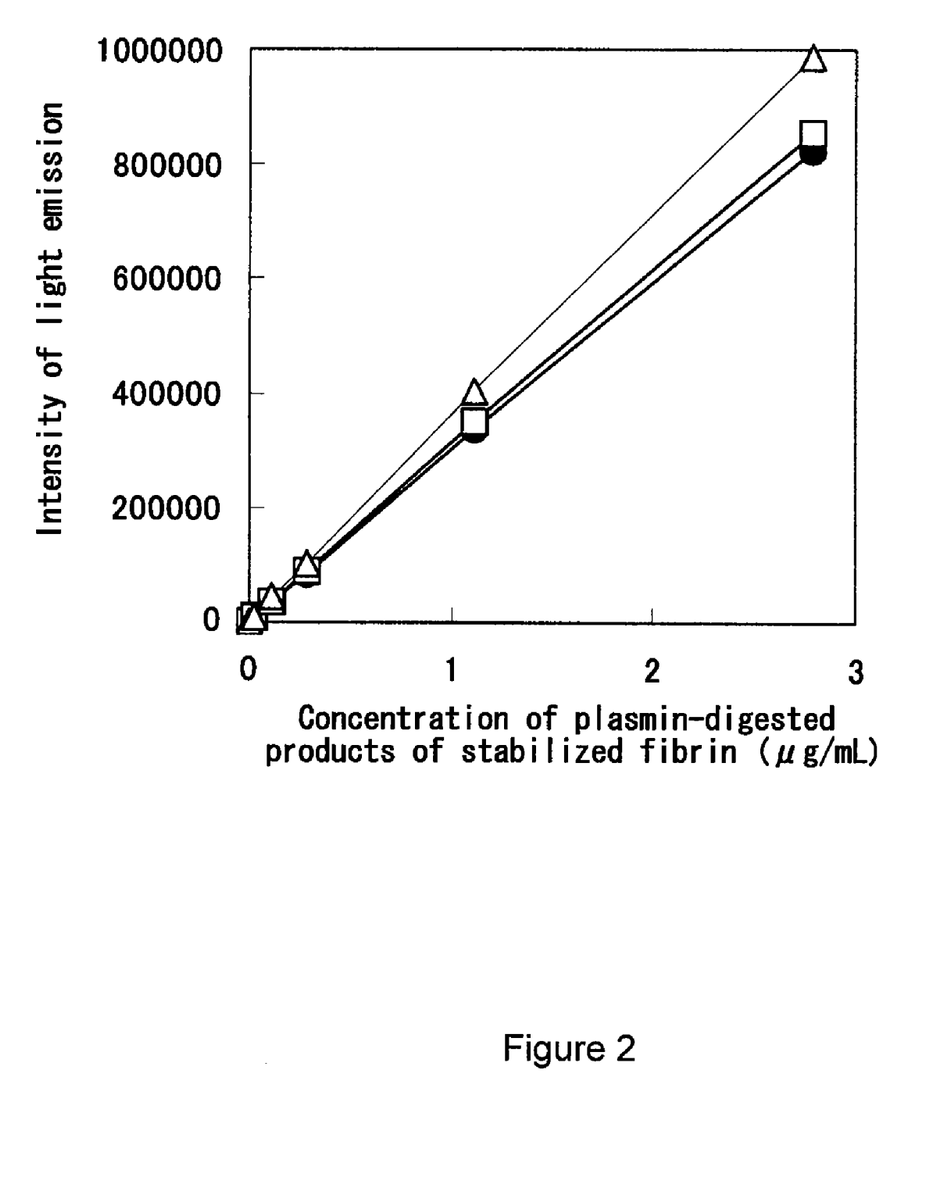
FIG. 2 is a graph showing the results of measuring a diluted series of plasmin-digested products of stabilized fibrin using three embodiments of the method of the present invention, that is, an embodiment using a combination of the JIF-23-antibody-immobilized magnetic particles and the alkaline-phosphatase-labeled No. 36-1 antibody (solid circles), an embodiment using a combination of the JIF-23-antibody-immobilized magnetic particles and the alkaline-phosphatase-labeled No. 1-1 antibody (open squares), and an embodiment using a combination of the JIF-23-antibodyimmobilized magnetic particles and the alkaline-phosphatase-labeled No. 5-4 antibody (open triangles).

FIG. 2 shows the results of measuring a diluted series of plasmin-digested products of stabilized fibrin using three embodiments of the method of the present invention, that is, an embodiment using a combination of the JIF-23-antibody-immobilized magnetic particles and the alkaline-phosphatase-labeled No. 36-1 antibody (solid circles in FIG. 2), an embodiment using a combination of the JIF-23-antibody-immobilized magnetic particles and the alkaline-phosphatase-labeled No. 1-1 antibody (open squares in FIG. 2), and an embodiment using a combination of the JIF-23-antibody-immobilized magnetic particles and the alkaline-phosphatase-labeled No. 5-4 antibody (open triangles in FIG. 2).

As apparent from the results of these combinations, the same reactivity as that of the combination using the No. 36-1 antibody was obtained, when antibodies that recognized a neoantigen in the E domain of stabilized fibrin were used as an antibody to be labeled with alkaline phosphatase. This result indicates that any antibody that recognized a neoantigen in the E domain of digested products of stabilized fibrin may be used as an antibody to be labeled with alkaline phosphatase.

Referential Example 1

Confirmation of Recognition Sites of Monoclonal Antibodies No. 36-1, No. 1-1, and No. 5-4

The reaction specificities of the monoclonal antibodies No. 36-1, No. 1-1, and No. 5-4 were determined by the method described in Example 5 of Japanese Examined Patent Publication (Kokoku) No. 5-48119, that is, by Western blotting in accordance with Zeta-Probe Blotting Mewbraues Instruction Manual (BioRad).

More particularly, fibrinogen was treated with plasmin in the presence of $Ca^{2+}$ or EGTA, and digested products of fibrinogen obtained after the reactions for 30 minutes, 60 minutes, and 24 hours were applied to an SDS polyacrylamide gel electrophoresis in the presence or absence of dithiothreitol (DTT) followed by Western blotting using the No. 36-1 antibody. This procedure was repeated, except that plasmin-digested products of stabilized fibrin, fragment D, or fragment E were used instead of the digested products of fibrinogen.

The results are shown in Table 1. In Table 1, the symbol (−) means that the antibodies do not have the binding reactivity, and the symbol (+) means that the antibodies have the binding reactivity. As shown in Table 1, it was confirmed that the antibodies No. 36-1, No. 1-1, and No. 5-4 reacted with a neoantigen which is newly exposed in the E domain by digesting stabilized fibrin with plasmin.

TABLE 1

| Antigens | Reactivity |
| --- | --- |
| Fibrinogen | (−) |
| X | (−) |
| Y | (+) |
| Fragment D dimer | (−) |
| (DD) E | (+) |
| early D | (−) |
| Dcate | (−) |
| Degta | (−) |
| Aα | (−) |
| Bβ | (−) |
| γ | (−) |
| γ-γ | (−) |
| 1γ5 | (−) |
| E1, E2 | (+) |
| E3 | (+) |

INDUSTRIAL APPLICABILITY

The immunological analyzing method of the present invention may be applied to various diagnoses, such as a diagnosis of DIC, DVT, or pulmonary embolism.

Although the present invention has been described with reference to specific embodiments, various changes and modifications obvious to those skilled in the art are possible without departing from the scope of the appended claims.

The invention claimed is:

1. A method of immunologically analyzing plasmin-digested products of stabilized fibrin, the method comprising:
    (a) bringing a sample suspected of containing plasmin-digested products of stabilized fibrin into contact with a first monoclonal antibody and a second monoclonal antibody,
    wherein the first monoclonal antibody does not form a sandwich immunocomplex with stabilized fibrin, fibrinogen, or plasmin-digested products of fibrinogen, but reacts with a neoantigen in a D domain of stabilized fibrin which is newly exposed by digesting stabilized fibrin with plasmin, and the second monoclonal antibody does not form a sandwich immunocomplex with stabilized fibrin, fibrinogen, or plasmin-digested products of fibrinogen, but reacts with plasmin-digested products of stabilized fibrin and a neoantigen that is newly exposed in an E domain by digesting stabilized fibrin with plasmin,
    wherein one of said first or second monoclonal antibodies is carried on a magnetic particle, and the other is labeled with an enzyme label;
    (b) separating enzyme-labeled monoclonal antibody which forms an immunocomplex via plasmin-digested products of stabilized fibrin with the monoclonal antibody carried on a magnetic particle from enzyme-labeled monoclonal antibody which does not form the immunocomplex;
    (c) adding a chemiluminescent substrate to the separated immunocomplex to generate a chemiluminescent signal; and
    (d) analyzing the generated chemiluminescent signal, wherein the amount of chemiluminescent signal correlates with the amount of plasmin-digested products of stabilized fibrin in the sample.

2. The method according to claim 1, wherein the chemiluminescent substrate is 1,2-dioxetane.

3. The method according to claim 1, wherein the enzyme label is alkaline phosphatase.

4. A kit for immunologically analyzing plasmin-digested products of stabilized fibrin, said kit comprising
  (a) a first monoclonal antibody which does not form a sandwich immunocomplex with stabilized fibrin, fibrinogen, or plasmin-digested products of fibrinogen, but binds to a neoantigen which is newly exposed in a D domain of stabilized fibrin by digesting stabilized fibrin with plasmin,
  (b) a second monoclonal antibody which does not form a sandwich immunocomplex with stabilized fibrin, fibrinogen, or plasmin-digested products of fibrinogen, but binds to plasmin-digested products of stabilized fibrin and a neoantigen that is newly exposed in an E domain of stabilized fibrin by digesting stabilized fibrin with plasmin, and
  (c) a chemiluminescent substrate,
  wherein one of the first or second monoclonal antibodies is carried on a magnetic particle, and the other is labeled with an enzyme label, a substrate of which is the chemiluminescent substrate.

5. A method of immunologically analyzing plasmin-digested products of stabilized fibrin, the method comprising:
  (a) bringing a sample suspected of containing plasmin-digested products of stabilized fibrin into contact with
    (i) a first monoclonal antibody that does not form a sandwich immunocomplex with stabilized fibrin, fibrinogen, or plasmin-digested products of fibrinogen, but binds to a first epitope on a neoantigen in a D domain of stabilized fibrin which is newly exposed by digesting stabilized fibrin with plasmin, and
    (ii) a second monoclonal antibody which does not form a sandwich immunocomplex with stabilized fibrin, fibrinogen, or plasmin-digested products of fibrinogen, but binds to plasmin-digested products of stabilized fibrin and a neoantigen that is newly exposed in an E domain of stabilized fibrin by digesting stabilized fibrin with plasmin, to form an immunocomplex of first monoclonal antibody-plasmin-digested products of stabilized fibrin-second monoclonal antibody, wherein said second monoclonal antibody carries a detectable label;
  (b) separating unbound second monoclonal antibody from said immunocomplex;
  (c) analyzing the amount of label in said sample, wherein the amount of label detected indicates the amount of plasmin-digested products of stabilized fibrin in said sample.

6. The method of claim 5, wherein said first monoclonal antibody is carried on a magnetic particle.

7. The method of claim 5, wherein said detectable label is an enzyme label.

8. The method of claim 7 further comprising the step of adding enzyme-specific chemiluminescent substrate to said immunocomplex.

* * * * *